United States Patent [19]
Funk

[11] Patent Number: 6,098,628
[45] Date of Patent: Aug. 8, 2000

[54] CLEAR PLASTIC EYE SHIELD

[76] Inventor: Donald E. Funk, 2833 S. Ponte Vedra Blvd., Ponte Vedra Bch, Fla. 32082

[21] Appl. No.: 09/340,544

[22] Filed: Jun. 28, 1999

[51] Int. Cl.$^7$ ....................................................... A61C 5/14
[52] U.S. Cl. ................................................. 128/859; 2/15
[58] Field of Search .................................. 128/846, 857, 128/858; 2/15, 11, 426

[56] References Cited

U.S. PATENT DOCUMENTS

| | | | |
|---|---|---|---|
| 4,709,695 | 12/1987 | Kohn | 128/858 |
| 4,862,902 | 9/1989 | Goffman | 128/858 |
| 4,867,146 | 9/1989 | Krupnick | 128/858 |
| 4,944,040 | 7/1990 | Riedel | 128/858 |
| 5,183,059 | 2/1993 | Leonardi | 128/858 |
| 5,740,550 | 4/1998 | Yavitz | 128/858 |
| 5,769,806 | 6/1998 | Radow | 128/858 |
| 5,931,799 | 8/1999 | Guastella | 128/858 |

Primary Examiner—Michael A. Brown
Attorney, Agent, or Firm—Arthur G. Yeager

[57] ABSTRACT

This invention provides eye-protecting shields or chambers that are sealed against the facial skin by an adhesive pliable foam or sponge rubber layer about a face conforming flange with a bulbous clear portion not touching eyelids or the eyelashes. The shields can be ventilated to the atmosphere through a planar flap outwardly of a flat cutout adjacent an outer corner of an eye. Access to the eye may be secured via openable flap for the introduction of medicaments to the eye. In a specific embodiment the access to environmental air may be controlled by a selective access valve and a moisture or medicant pad may be carried by the flap inwardly of the shield. A releasable catch between the flap and the bulbous portion permits self-closing and retention of the flap. A pair of shields with an elastic member therebetween provides a pair of spectacles which may include an elastic or adjustable headband with releasable fastener(s).

30 Claims, 5 Drawing Sheets

CLEAR PLASTIC EYE SHIELD

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Field of the Invention

This invention relates to a protective covering for the human eye during medical treatment; and more particularly, a protective shield or chamber for the eye following surgery.

2. Description of the Related Art

At the present time patients undergoing eye surgery are provided with a plastic bubble-shaped transparent cover for an eye, the cover having a planar border portion being fastened to the facial skin around the eye with adhesive tape. There is no ventilation through the cover, and it must be removed for the administration of medicaments to the eye, followed by taping to seal the cover to the eye. If ventilation is desired a single hole normally is punched through the bubble portion. A prior patent to describe this type of shield is U.S. Pat. No. 5,740,550, issued to E. Q. Yavitz.

BRIEF SUMMARY OF THE INVENTION

This invention provides an eye protecting shield or chamber that comprises a transparent bulbous cover that does not touch any part of the eye and is sealed to the face of the wearer about the perimeter of the chamber by a spongy rubber or plastic foam layer and a double sided adhesive collar applied thereto. Rather than the adhesive, a suitable headband may be affixed to the shield. In one embodiment the chamber is ventilated by a pattern of small holes near the outer corner of the eye. A hinged access that is selectively openable permits medicaments to be placed in the eye without otherwise disturbing the seal around the chamber. The shield may be a single one for one eye or a double one for both eyes. In another embodiment a moisture or medicament pad is carried by the hinged access of the shield and a air valve controls the flow of air through the pad and air/moisture escaping from the chamber.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF THE INVENTION

Figure 1:
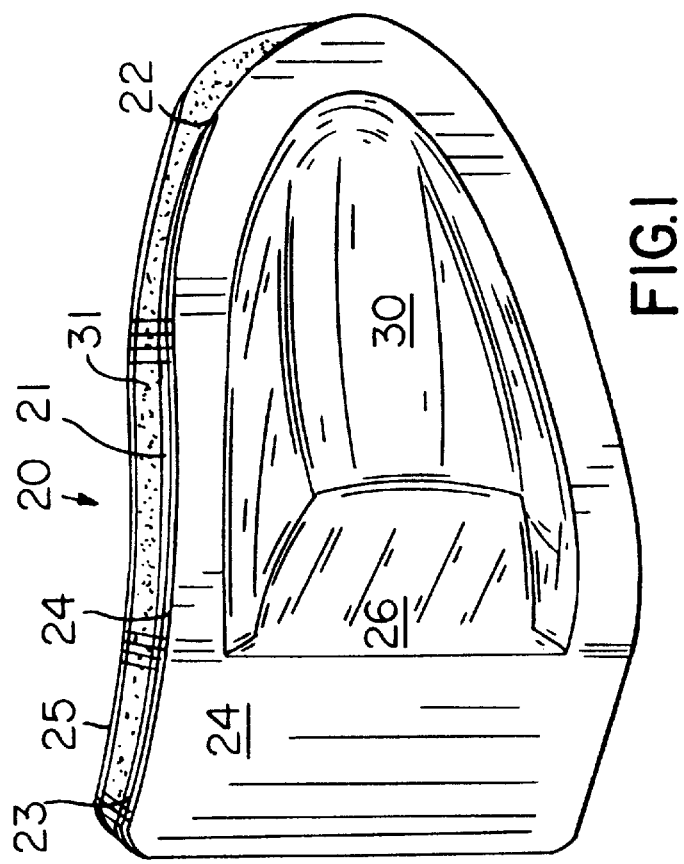
FIG. 1 is a bottom perspective view of the first embodiment of the attachable eye protective shield for the left human eye in accord with the present invention; the shield for the right human eye being the mirror image thereof.
Figure 2:
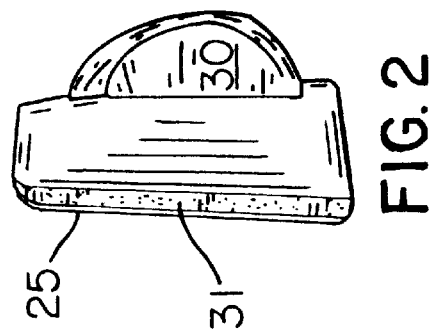
FIG. 2 is a right end elevational view of the eye shield of FIG. 1.
Figure 3:
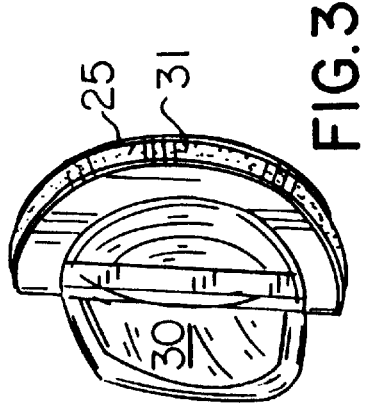
FIG. 3 is a left end elevational view of the eye shield of FIG. 1.
Figure 6:
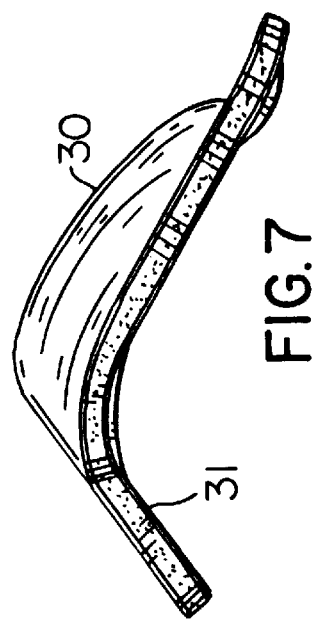
FIG. 6 is a top plan view of the eye shield of FIG. 1.
Figure 7:
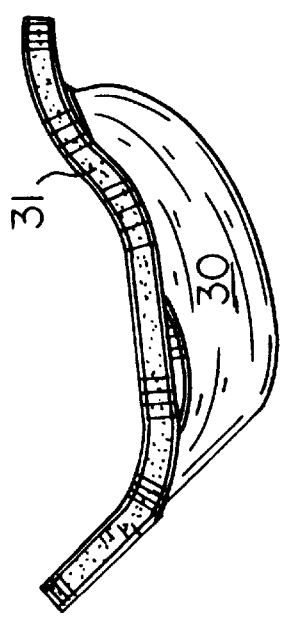
FIG. 7 is a bottom plan view of the eye shield of FIG. 1.
Figure 4:
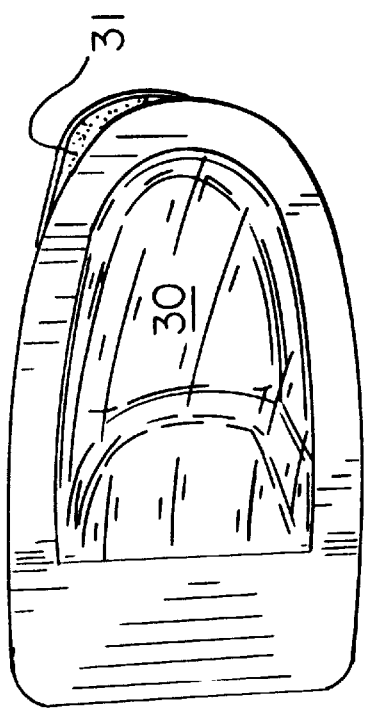
FIG. 4 is a front elevational view of the eye shield of FIG. 1.
Figure 5:
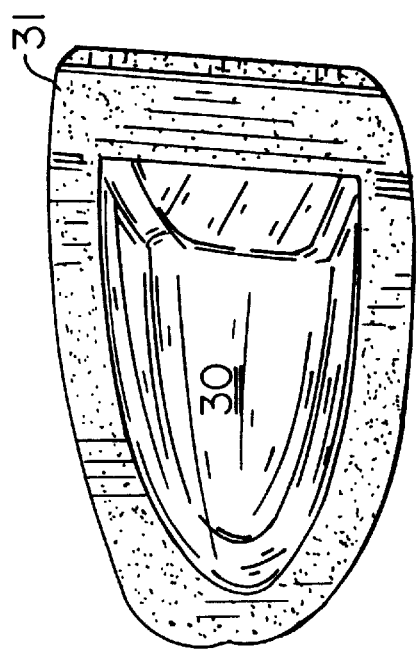
FIG. 5 is a rear elevational view of the eye shield of FIG. 1.

This invention relates to the field of medical surgery on the human eye, and especially to eye protectors in the form of a single or double eye chambers or shields that are worn after surgery to protect the eye from outer forces and contamination while providing optional means for introducing medicinal preparations into the eye and maintaining the proper moisturizing atmosphere for the healing of one or both eyes. There are several embodiments of this invention, and two forms to each embodiment, e.g., the use of one chamber for one eye or the use of two chambers for two eyes. The embodiments relate to ways and means to expose the eye for the introduction of medications and for providing a moisturizing atmosphere for the eye without disturbing the protective covering of the chamber. The accompanying drawings show these embodiments.

In FIGS. 1–7 there are views of the eye showing the shield or chamber 20 including a contoured flange portion 21 with a tapering portion 22 adjacent the nose of a face and an enlarged portion 23 adjacent the temple.

Flanged portion 21 forms a border around a clear eyepiece 30 and a skin colored plastic member 24 covers the flange portion on the outside of shield 20. Eyepiece 30 projects outwardly from the face so as not to touch the eyelashes or eyelids or otherwise interfere with the healing of the eye. The chambers or shields in the embodiments of FIGS. 1–7 merely cover the eyes and do not, provide any special access to the eye for the introduction of medication or moisture as later described with respect to FIGS. 8–13. The chamber or shield 20 comprises a transparent plastic eyepiece 30 for an eye or may be in the form of a pair of shields 50, 51 as illustrated in FIG. 14. Each chamber or shield 20 includes a perimetric elastomeric seal of rubber or plastic foam 31 which rests against the face and holds the plastic transparent portion away from the face and extends laterally as a shield over the entire eye. There is a sloping substantially flat planar portion 26 near the outer corner of the eye which may or may not be perforated with a pattern of ventilation holes 33 in different embodiments of this invention. A double-sided adhesive tape 25 is preferably employed between foamed seal 31 and the patient's face in order to hold the single shield 20 or double shields 50, 51 in place. Several double-sided tapes 25 may be provided with release papers on each side for affixation to the exposed adhesive on the foam 31 when it no longer will firmly seal to the face.

Figure 8:
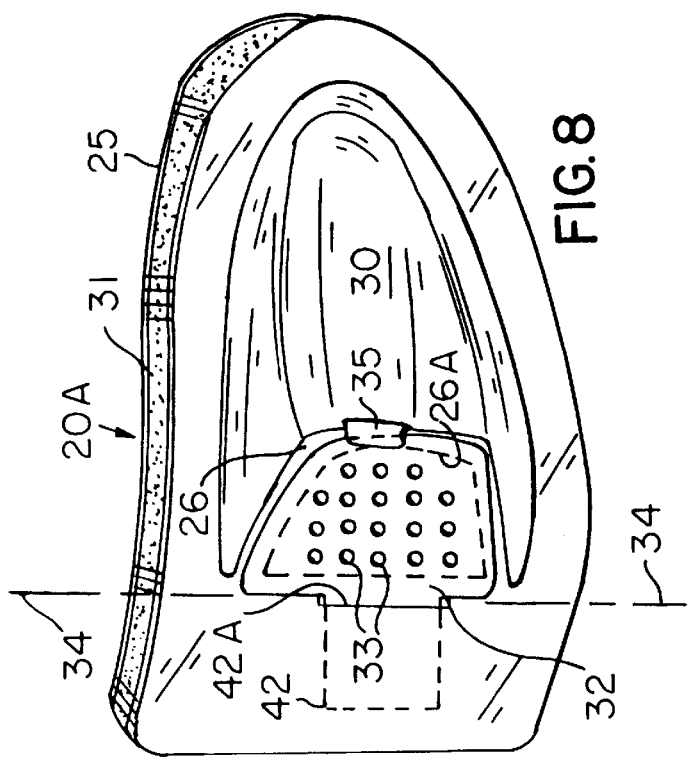
FIG. 8 is a top perspective view of the second embodiment of the attachable eye shield for the left human eye in accord with the present invention; the shield for the right eye being the mirror image thereof.
Figure 9:
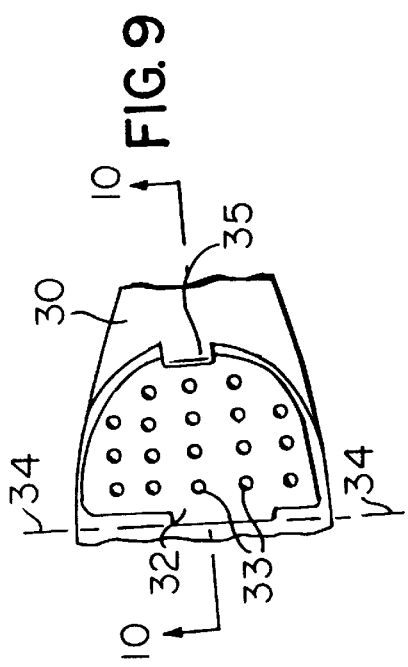
FIG. 9 is an enlarged front elevational partial view of the flat planar portion of eye shield of FIG. 8.
Figure 10:
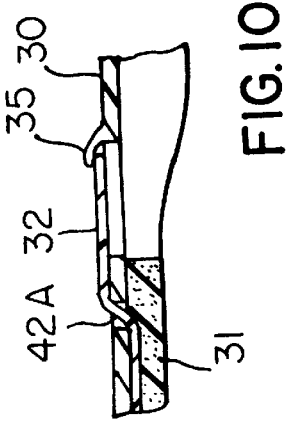
FIG. 10 is a cross-sectional view taken along line 10—10 of FIG. 9.

FIGS. 8–10 illustrate a second embodiment of this invention showing how eye shield 20A may be employed to provide ventilation for the eye and may be used to introduce medication to the eye without removal of shield 20 from facial attachment. In this embodiment flat portion 26 contains a void or cut out 26A and is replaced by an extended plastic flap portion 32 which is pierced with a pattern of holes 33 to provide access to the eye while the shield 20 remains attached to the face. To insure proper ventilation, a plurality of at least nine spaced holes 33 of not more than about 0.06 inches should be provided. In addition there is a tongue or catch 35 that retains portion 32 closed when it is not open to receive medication for the eye. The bendable flap portion 32 includes a tab 42 which extends through slot 42A and is affixed to the inside of flange 21 before the seal 31 is applied thereto. The skin colored member 24 depicted in FIG. 1 is optionally applied on the outside of flange 21. Other than those differences, this embodiment is identical to the embodiment of FIGS. 1–7. The hinged perforate portion 32 includes means for selectively opening and closing same which herein is defined by a tongue or catch 35 which extends beyond the edge of cutout 26A of flat portion 26 so that the flap portion 32 may be temporarily bent to fit beneath catch 35 and released. Other opening and closing means may be employed for the preferred means herein disclosed, e.g., a suitable adhesive, a releasable fastener or the like without departing from the spirit of the invention.

Figure 11:
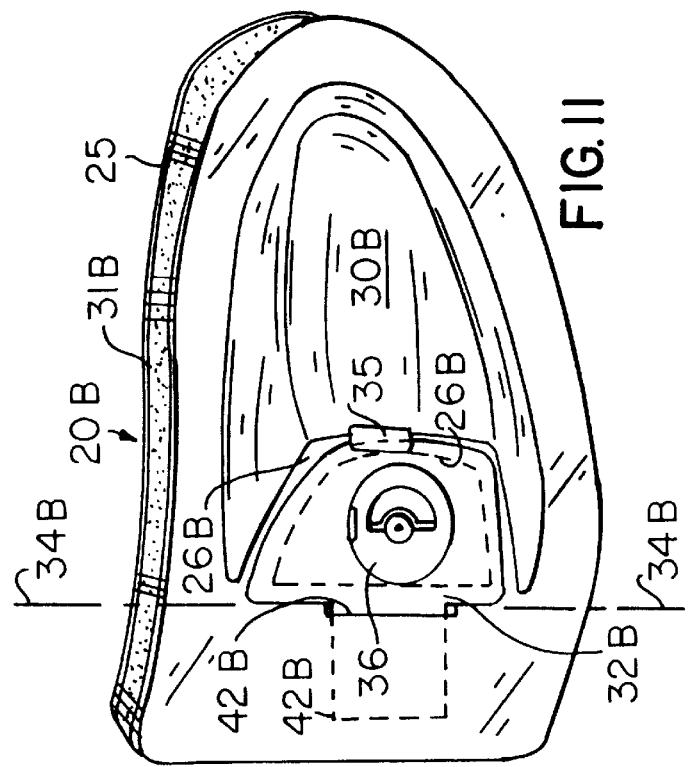
FIG. 11 is a front perspective view of the third embodiment of the attachable eye for the left human eye in accord with my new invention; the shield for the right human eye being the mirror image thereof.
Figure 12:
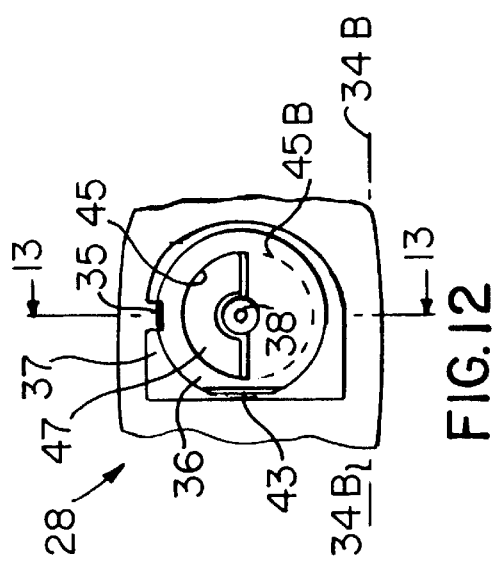
FIG. 12 is an enlarged front elevational view of the valve in the flat planar portion of the shield of FIG. 11.
Figure 13:
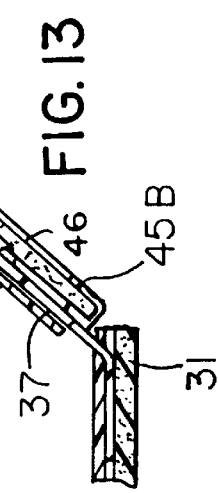
FIG. 13 is a cross-sectional taken along line 13—13 of FIG. 12.
Figure 14:
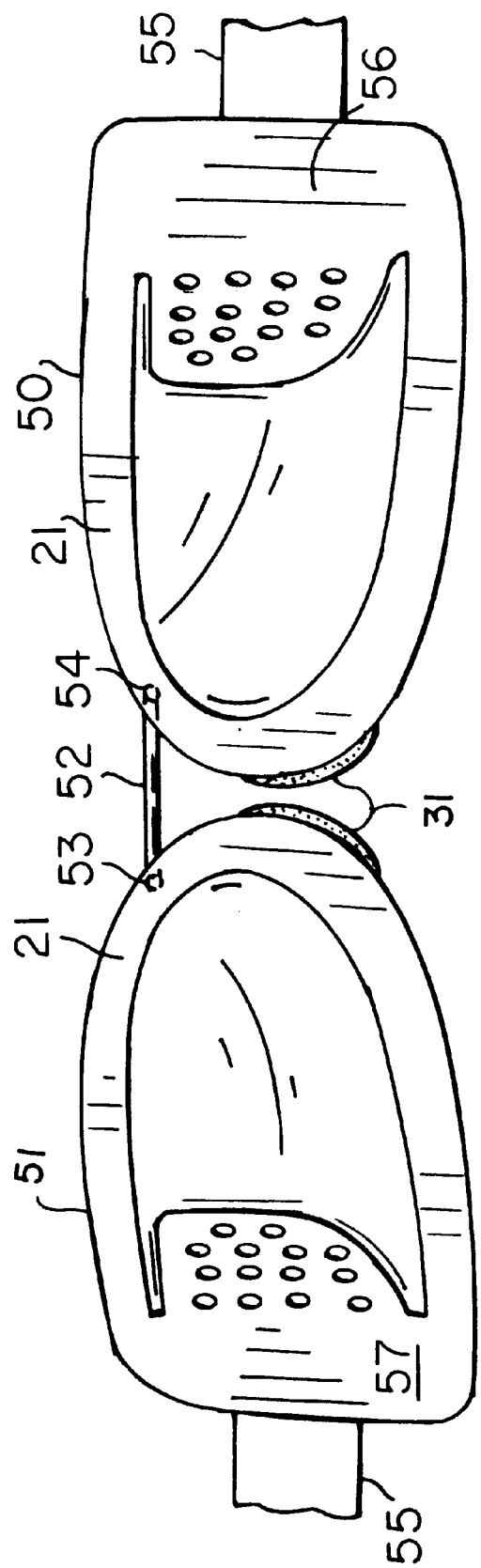
FIG. 14 is a top plan view of a pair a spectacle shields for two eyes according to this invention.

A third embodiment of the invention is shown in FIGS. 11–13 of the drawings. In this embodiment the sloping flap portion 32B of member 24B of the shield 20B includes an adjustable ventilation valve 28. Valve 28 comprises a plurality of stacked plates or discs mounted parallel to each other about a central pivot 38, which in a preferred arrangement is actually a rivet holding the plates and discs together onto flap portion 32B. At the innermost end of this arrangement is a double-walled support 44 forming a pocket 46. Outwardly of support 44 is immovable valve plate 37 formed by flap portion 32B. Next to plate 37 is a movable throttle disc 36, all as shown in FIG. 13. Each of these plates and discs is pierced with one or two openings 45 which can be aligned with each other to have an open passageway for air or which may be throttled down to reduce the volume of flow and/or to substantially close same. The inside wall 44 of pocket 46 may have an enlarged opening 45A to enhance ventilation. The entire group of plates and discs is pivotable or hinged about axis 34B to permit access to the eye when desired. A tongue or catch 35, as previously described with respect to FIGS. 8–10, is employed to allow the entire group of plates and discs to be opened or closed for access to the eye. To be partially open the catch 35 may be disengaged with the flap portion 32B and when substantially closed would be outwardly of and engaged with flap portion 32B. Control of the air allowed into or out of the eyepiece is accomplished by turning disc 36, by finger handle or tab 43, about its pivot 38 to open or close the air passage through those controls. Tab 43 is connected to disc 36 to open or close those air passages or to selectively partially open same. The pocket 46 by the envelope walls of double-walled support 44 is filled with felt, fibrous cotton, lint free sponge, or other porous textile 47 into which medication may be dripped and eventually evaporated into the eye to assist in healing thereof.

FIG. 14 depicts another embodiment of a pair of shields 50, 51 connected together adjacent a bridge of a nose by an expansible and contractible member 52 in the form of a fabric covered elastic well known to those skilled in the art, such member providing an adjustable fit of the shields 50, 51 on various size and contours of faces which may wear same. Member 52 may be connected to shields 50, 51 by passing through holes 53 and 54 and glued between flanged portions 21 and seals 31. The headband 55 may be affixed to shields 50, 51 in any convenient manner as by adhesive between flanged portions 21 and seals 31, or looped through generally vertical slots adjacent the edge portions 56, 57 and affixed to itself. The headband may be elastic or of any suitable material with a releasable fastener to permit adjustability., such as Velcro, or a series of spaced snaps or the like.

Of course, any of the embodiments described herein may be made into a pair in much the same manner as that shown in FIG. 14. While not believed to be practical or desirable, the flat portion 26 of the shield 20 of FIGS. 1–7 may be formed with a plurality of spaced holes, like 33 of FIG. 8, but access to the eye as described with respect to FIGS. 8–10 would not be provided and the costs of production would be substantial.

While the invention has been described with respect to certain specific embodiments, it will be appreciated that many modifications and changes may be made by those skilled in the art without departing from the spirit of the invention. It is intended therefore, by the appended claims to cover all such modifications and changes as fall within the true spirit and scope of the invention.

What is claimed as new and what it is desired to secure by Letters Patent of the United States is:

1. An eye-protecting shield comprising an elongated transparent eyepiece extending laterally over the eye of a human and spaced outwardly away from an eyeball and eyelids and fitting along its outer perimeter to facial skin adjacent an eye substantially between a nose and a temple of a human, said eyepiece having an elongated bulbous portion tapering to a smaller portion adjacent an inner portion of an eye toward a nose and an enlarged portion adjacent an outer portion of an eye covered thereby, said enlarged portion having a substantially first planar portion at an end of said bulbous portion, said shield having a flange about said bulbous portion, said flange conforming generally to a contour of a face about an eye and having a substantially second planar portion coplanar with said first planar portion, and means to seal said flange to a face.

2. The shield of claim 1 having a plurality of spaced air passages through said first planar portion.

3. The shield of claim 2 wherein said plurality comprises at least nine holes, each having a diameter of not more than 0.06 inch.

4. The shield of claim 2 wherein said first planar portion contains a cut-out to provide access to an eye, said eyepiece including a planar flap hingedly attached to said flange near an outer corner of an eye to overlie said cut-out so as to permit access therethrough when said flap is opened.

5. The shield of claim 4 in which said planar flap includes a plurality of spaced air passages therethrough communicating with said cut-out to provide air passageways through said eyepiece.

6. The shield of claim 4 wherein said planar flap includes adjustment means for controlling ventilation of an eye covered by said shield.

7. The shield of claim 6 wherein said adjustment means includes a valve disc having at least one opening therethrough and said flap having at least one opening therethrough, said at least one openings being aligned when said valve disc is in its fully opened condition, said disc and flap blocking respective said at least one openings of respective said flap and disc when said valve disc is in its fully closed condition.

8. The shield of claim 7 wherein said adjustment means includes a pivot attached to said flap and pivotally attaches said disc to said flap, said disc being rotatable at least through about 180 degrees, said at least one openings being less then about 180 degrees and cooperate to provide an adjustable sized passageway through said shield for access to an eye without removal of said shield from a face.

9. The shield of claim 7 further comprising a pocket attached to said flap inwardly of said shield, said pocket being adapted to carry a moisture or medicant receiving pad disposable in general alignment with and underlying said at least one opening in said flap.

10. The shield of claim 9 further comprising latching means on said bulbous portion to releasably retain said flap in closing position overlying said cut-out.

11. The shield of claim 1 wherein said first planar portion includes a cut-out, said eyepiece including a planar flap hingedly attached to said bulbous portion, latching means between said first planar portion and said planar flap to releasably retain said flap in closing position overlying said cut-out.

12. The shield of claim 11 wherein said flap includes a plurality of spaced air passages communicating through said cut-out interiorly of said bulbous portion.

13. The shield of claim 11 further comprising an adjustment means for controlling ventilation through said flap of an eye covered by said shield.

14. The shield of claim 13 wherein said adjustment means includes a rotatable valve having at least one opening therethrough selectively communicating with at least one opening through said flap.

15. The shield of claim 14 further comprising a pocket attached to said flap inwardly of said bulbous portion, said pocket adapted to carry a moisture or medicant pad therein so that air may pass therethrough from said at least one openings when aligned or partially aligned.

16. The shield of claim 1 wherein said means to seal includes a compressible conforming foam material attached to said flange.

17. The shield of claim 1 wherein said means to seal includes a double-sided adhesive.

18. The shield of claim 1 comprising another shield in accord with claim 1, said shield and another shield being formed into a pair of spectacles, and bridge means connecting said shield and another shield together.

19. The shield of claim 18 wherein said bridge means includes an expansible and contractable member to permit attachment of said pair of spectacles to differing size and contours of faces.

20. The shield of claim 18 wherein said shield and another shield are mirror images of each other.

21. An eye-protecting shield comprising a body member extending laterally over the eye of a human and spaced outwardly away from an eyeball and eyelids and fitting along its outer perimeter to the facial skin adjacent an eye substantially between a nose and temple of a human, an elongated bulbous portion having opposite end portions, one said end portion of said bulbous portion being adjacent a nose and terminating on said body member, said other end portion of said bulbous portion terminating in an enlarged opening, and a flap attached to said body member operable between an open and closed position for selectively covering and uncovering said opening.

22. The shield of claim 21 wherein said flap includes a hinged portion formed integral to said flap, said flap being selectively movable on said hinge portion between an open position and a closed position.

23. The shield as defined in claim 22 further including a plurality of spaced openings formed in said flap to provide ventilation of an eye.

24. The shield as defined in claim 22 wherein said flap further includes cooperating securing means mounted between said flap and said bulbous member for selectively securing said flap in said closed position.

25. The shield as defined in claim 22 wherein said flap includes at least one opening therethrough to provide for ventilation to an eye.

26. The shield as defined in claim 22 wherein said flap includes at least one opening therethrough to provide for ventilation to an eye, said flap including a planar member, at least one ventilation control valve carried by said flap and positioned over said at least over said at least one opening, and valve open and closed position.

27. The shield as defined in claim 21 wherein said flap includes a planar member, at least one ventilation control valve carried by said flap and being selectively operable between an open and closed position.

28. The shield of claim 21 wherein said flap includes a hinged portion formed integral to said flap, said flap being selectively movable on said hinge between an open position and a closed position, a plurality of spaced openings formed in said flap to provide ventilation of an eye, and said flap further including cooperating securing means mounted between said flap and said bulbous member for securing said flap in said closed position.

29. The shield of claim 21 further comprising an adjustment means for controlling ventilation through said flap of an eye covered by said shield, an adjustment means including a rotatable valve having at least one opening therethrough selectively communicating with at least one opening through said flap.

30. The shield of claim 21 comprising another shield in accord with shield and another shield in accord with claim 21, said shield and another shield being formed into a pair of spectacles, and elastic means connecting said shield and another shield together for adjusting to different size faces, and a headband connected to said pair of spectacles.

* * * * *